US009671492B2

(12) United States Patent
Diewald (10) Patent No.: US 9,671,492 B2
(45) Date of Patent: Jun. 6, 2017

(54) RADAR SENSING OF VEHICLE OCCUPANCY (71) Applicant: IEE International Electronics & Engineering S.A., Echternach (LU)

(72) Inventor: Andreas Diewald, Waldweiler (DE)

(73) Assignee: IEE International Electronics & Engineering S.A., Echternach (LU)

(*) Notice: Subject to any disclaimer, the term of this patent is extended or adjusted under 35 U.S.C. 154(b) by 0 days.

(21) Appl. No.: 14/912,379

(22) PCT Filed: Aug. 13, 2014

(86) PCT No.: PCT/EP2014/067320
§ 371 (c)(1),
(2) Date: Feb. 16, 2016

(87) PCT Pub. No.: WO2015/022358
PCT Pub. Date: Feb. 19, 2015

(65) Prior Publication Data
US 2016/0200276 A1 Jul. 14, 2016

(30) Foreign Application Priority Data
Aug. 14, 2013 (LU) .......................... 92268

(51) Int. Cl.
G01S 13/56 (2006.01)
G01S 7/35 (2006.01)
(Continued)

(52) U.S. Cl.
CPC ........ *G01S 13/56* (2013.01); *B60R 21/01534* (2014.10); *G01S 7/354* (2013.01);
(Continued)

(58) Field of Classification Search
CPC . B60R 21/01534; B60R 21/015; G01S 13/04; G01S 13/56; G01S 7/354;
(Continued)

(56) References Cited

U.S. PATENT DOCUMENTS 4,739,331 A 4/1988 Pincoffs et al.
6,220,627 B1* 4/2001 Stanley ................. B60R 21/015
180/272

(Continued)

FOREIGN PATENT DOCUMENTS

CN 1898928 A 1/2007

OTHER PUBLICATIONS

International Search Report issued Nov. 10, 2014 re: Application No. PCT/EP2014/067320; pp. 1-3; citing: US 2005/073424 A1, U.S. Pat. No. 4 739 331 A and US 2003/201894 A1.
(Continued)

*Primary Examiner* — Matthew M Barker
(74) *Attorney, Agent, or Firm* — Reising Ethington P.C.

(57) ABSTRACT

A method for sensing occupancy status within an automotive vehicle uses a radar sensor system, the radar sensor system includes an antenna system, at least one sensor and processing circuitry. The method comprises illuminating, using the antenna system, at least one occupiable position within the vehicle with continuous wave (CW signals), the CW signals being frequency modulated in time. At least one sensor signal ($y(t,f_1) \ldots y(t,f_n)$) reflected as a result of the CW signals, is received using at least one sensor the at least one sensor defining a plurality of receive channels (1 ... i), each channel having a different frequency ($f_1 \ldots f_i$). Processing circuitry is operable for applying, for each receive channel (1 ... i), DC offset removal to the corresponding sensor signal ($y(t,f_1) \ldots y(t,f_n)$) to generate a modified signal ($y'(t,f_1) \ldots y'(t,f_n)$); and generating, based on the modified signals
(Continued)

(y'(t, f$_1$) ... y'(t,f$_n$)) one or more occupancy status signals, the occupancy status signal indicating a property related to said at least one occupiable position.

14 Claims, 8 Drawing Sheets

(51) Int. Cl.
  *G01S 7/41* (2006.01)
  *G01S 13/34* (2006.01)
  *B60R 21/015* (2006.01)
  *A61B 5/05* (2006.01)
  *A61B 5/00* (2006.01)
  *G01S 13/88* (2006.01)

(52) U.S. Cl.
  CPC .............. *G01S 7/415* (2013.01); *G01S 13/34* (2013.01); *A61B 5/05* (2013.01); *A61B 5/6893* (2013.01); *B60R 21/015* (2013.01); *G01S 13/88* (2013.01)

(58) Field of Classification Search
  CPC .......... G01S 7/415; G01S 13/34; G01S 13/88; A61B 5/6893; A61B 5/05
  See application file for complete search history.

(56) References Cited

U.S. PATENT DOCUMENTS

| | | | |
|---|---|---|---|
| 6,252,240 B1 * | 6/2001 | Gillis | G01G 19/4142 250/221 |
| 6,266,592 B1 * | 7/2001 | LeMense | B60N 2/0276 180/271 |
| 6,290,255 B1 * | 9/2001 | Stanley | B60R 21/01536 180/271 |
| 6,302,438 B1 * | 10/2001 | Stopper, Jr. | B60R 21/0154 280/735 |
| 6,348,862 B1 * | 2/2002 | McDonnell | B60N 2/002 180/272 |
| 6,429,774 B1 * | 8/2002 | Schmid | B60R 21/01534 340/426.28 |
| 6,445,294 B1 * | 9/2002 | McDonnell | B60N 2/002 180/272 |
| 6,598,900 B2 * | 7/2003 | Stanley | B60N 2/286 280/735 |
| 6,753,780 B2 | 6/2004 | Li | |
| 6,792,057 B2 * | 9/2004 | Kabel | H03H 17/0266 375/240 |
| 7,090,247 B2 * | 8/2006 | Hofbeck | B60R 21/01534 280/735 |
| 7,196,629 B2 * | 3/2007 | Ruoss | A61B 5/0507 280/734 |
| 7,315,002 B2 * | 1/2008 | Hofbeck | B60R 21/01534 177/136 |
| 7,520,529 B2 * | 4/2009 | Hofbeck | B60R 21/01534 280/735 |
| 7,835,261 B2 | 11/2010 | Alliot et al. | |
| 7,907,082 B2 * | 3/2011 | Antonsson | G01S 7/282 342/27 |
| 8,665,137 B2 * | 3/2014 | Wintermantel | G01S 7/032 342/188 |
| 8,816,902 B2 * | 8/2014 | Itoh | G01S 3/74 342/104 |
| 2003/0201894 A1 | 10/2003 | Li | |
| 2004/0020314 A1 * | 2/2004 | Tsuchihashi | A61B 5/0507 73/865.9 |
| 2005/0073424 A1 | 4/2005 | Ruoss et al. | |
| 2016/0001728 A1 * | 1/2016 | Schrabler | B60R 21/01534 342/28 |

OTHER PUBLICATIONS

Written Opinion issued Nov. 10, 2014 re: Application No. PCT/EP2014/067320; pp. 1-7; citing: US 2005/073424 A1.
Chinese Office Action in Chinese with English translation for CN application No. 201480045156, dated Dec. 14, 2016, 18 pages.

* cited by examiner

RADAR SENSING OF VEHICLE OCCUPANCY

TECHNICAL FIELD

The present invention generally relates to the technical field of sensing objects internal to a vehicle, and more specifically to FMCW radar sensing for detecting occupants in a vehicle.

BACKGROUND ART

State of the art systems for occupant classification and detection are foil based systems which are integrated in every single seat (involving high integration costs). It is also known to provide for contactless sensing (e.g. of humans) within a vehicle, e.g. for occupancy detection (OD), occupancy classification (OC) or seat-belt reminder (SBR) functionality. Radar based in-vehicle systems are not established on the market due to high costs. In general, each single seat needs a separate radar sensor.

Radar technology offers some advantages in comparison to other occupancy detection and classification methods. It is a contactless and invisible measurement system which can easily be integrated behind plastic covers and textiles. Radar systems can measure the smallest motions within the range of micrometers. Existing state of the art solutions use a conventional single frequency Doppler radar as a motion sensor. This is not sufficient in order to get a reliable indication of the occupancy status or of whether the human is inside or outside the car.

BRIEF SUMMARY

An improved radar sensor for occupancy detection is herein provided.

According to one aspect of the invention there is provided a method for sensing occupancy status within an automotive vehicle using a radar sensor system, the radar sensor system comprising an antenna system, at least one sensor and processing circuitry, the method comprising:

illuminating, using the antenna system, at least one occupiable position within the vehicle with continuous wave (CW signals), the CW signals being frequency modulated in time;

receiving, using at least one sensor, at least one sensor signal ($\underline{y}(t, f_1) \ldots \underline{y}(t, f_n)$) reflected as a result of the CW signals, the at least one sensor defining a plurality of receive channels (1 . . . i), each channel having a different frequency (f1 . . . fi), operating the processing circuitry for applying, for each receive channel, DC offset removal to the corresponding sensor signal ($\underline{y}(t, f_1) \ldots \underline{y}(t, f_n)$) to generate a modified signal ($\underline{y}'(r, f_1) \ldots \underline{y}'(t, f_n)$); and generating, based on the modified signals ($\underline{y}'(t, f_1) \ldots \underline{y}'(t, f_n)$), one or more occupancy status signals, the occupancy status signal indicating a property related to said at least one occupiable position.

The one or more occupancy status signals may comprise an occupant detection signal, indicating whether or not an occupant is present in the occupiable position, an occupant classification signal, indicating a classification for an occupant present in the occupiable position, and/or an occupant vital signs signal, indicating the extent to which vital signs are exhibited in the occupiable position or by an occupant in the occupiable position.

The method may comprise operating the processing circuitry for generating a composite signal ($\underline{y}'(t, r)$) based on the sensor signals from all receive channels.

The method may comprise generating a composite signal comprises performing a FFT based on said modified signals.

The method may comprise operating the processing circuitry for generating a plurality of first intermediate signals ($\underline{A}_1 e^{-j2k_0x_1(t)} \ldots \underline{A}_m e^{-j2k_0x_m(t)}$) in the time domain, each first intermediate signal corresponding to a candidate object.

The method may comprise operating the processing circuitry for performing object separation and exterior object subtraction based on said composite signal ($\hat{\underline{y}}'(t, r)$).

The method may comprise operating the processing circuitry for performing, for each channel, a circle estimation operation on a signal comprising or based upon a respective sensor signal ($\underline{y}(t, f_1) \ldots \underline{y}(t, f_n)$) and outputting second intermediate signals.

The DC offset removal may be performed by a DC offset removal module.

The method may comprise operating the processing circuitry for (i) performing the circle estimation before said DC offset removal, whereby said circle estimation operation is performed on a respective sensor signal ($\underline{y}(t, f_1) \ldots \underline{y}(t, f_n)$), or (ii) performing said DC offset removal before the circle estimation, whereby said circle estimation operation is performed on a respective modified signal ($\underline{y}'(t, f_1) \ldots \underline{y}'(t, f_n)$).

The method may comprise operating the processing circuitry for receiving said second intermediate signals and deriving therefrom, the average over N receive channels of the radius value (R-value) of the circle estimation for the receive channels, and output third intermediate signals.

The method may comprise operating the processing circuitry for receiving the first intermediate signals ($\underline{A}_1 e^{-j2k_0x_1(t)} \ldots \underline{A}_m e^{j1\ j2k_0x_m(t)}$) or for receiving the third intermediate signals and generating therefrom, the one or more occupancy status signals.

In one embodiment, said occupancy status signal comprises an occupant detection signal; and the method comprises operating the processing circuitry for to generate and/or output (i) an occupant detection signal dependent upon a magnitude component of the first intermediate signals, (ii) a positive occupant detection signal when a sum of vectors derived from the magnitude component of the first intermediate signals is greater than a minimum threshold ($th_{min}$), and/or (iii) a negative occupant detection signal when a sum of vectors derived from the magnitude component of the first intermediate signals is less than a maximum threshold ($th_{max}$).

In one embodiment, said occupancy status signal comprises a vital signs signal; and the method comprises operating the processing circuitry for to generate and/or output the vital signs signal dependent upon a time-varying component ($x(t)$) of the first intermediate signals.

The method of any of the preceding claims, wherein the method comprises operating the processing circuitry for applying a buffer strategy to the modified signals ($\underline{y}'(t, f_1) \ldots \underline{y}'(t, f_n)$), or signals based thereon, whereby hysteresis is exhibited by the one or more occupancy status signals.

In one embodiment, the at least one occupiable position comprises one of a plurality of occupiable positions on a bench seat, and more preferably comprises 2 or 3 occupiable positions.

According to another aspect of the invention there is provided a programmable radar sensor system when suitably programmed for carrying out the method of any of claims 1 to 11 of the appended claims for sensing occupancy status within an automotive vehicle, the radar sensor system comprising an antenna system, at least one sensor and processing circuitry for performing the method.

According to another aspect of the invention there is provided a radar sensor system for sensing occupancy status within an automotive vehicle, the system comprising: an antenna system, for illuminating at least one occupiable position within the vehicle with continuous wave (CW signals), the CW signals being frequency modulated in time; at least one sensor for receiving at least one sensor signal ($\underline{y}(t, f_1) \ldots \underline{y}(t, f_n)$) reflected as a result of the CW signals, the at least one sensor defining a plurality of receive channels (1 ... i), each channel having a different frequency (f1 ... fi), processing circuitry, coupled to the at least one sensor, the processing circuitry being operable for applying, for each receive channel, DC offset removal to the corresponding sensor signal ($\underline{y}(t, f_1) \ldots \underline{y}(t, f_n)$) to generate a modified signal ($\underline{y}'(t, f_1) \ldots \underline{y}'(t, f_n)$); and generating, based on the modified signals ($\underline{y}'(t, f_1) \ldots \underline{y}'(t, f_n)$), one or more occupancy status signals, the occupancy status signal indicating a property related to said at least one occupiable position.

The one or more occupancy status signals may comprise an occupant detection signal, indicating whether or not an occupant is present in the occupiable position, an occupant classification signal, indicating a classification for an occupant present in the occupiable position, and/or an occupant vital signs signal, indicating the extent to which vital signs are exhibited in the occupiable position or by an occupant in the occupiable position.

The processing circuitry may include a transform module operable for: generating a composite signal ($\tilde{y}'(t, r)$) based on the sensor signals from all receive channels.

The transform module may comprise a FFT module operable to generate said composite signal based on said modified signals.

The processing circuitry may include an object separation and exterior object subtraction module operable for generating a plurality of first intermediate signals ($\underline{A}_1 e^{-j2k_0 x_1(t)} \ldots \underline{A}_m e^{-j2k_0 x_m(t)}$) in the time domain, each first intermediate signal corresponding to a candidate object.

The processing circuitry may be operable for performing said object separation and exterior object subtraction based on said composite signal ($\tilde{y}'(t, r)$).

The processing circuitry may include a circle estimation module operable for performing, for each channel, a circle estimation operation on a signal comprising or based upon a respective sensor signal ($\underline{y}(t, f_1) \ldots \underline{y}'(t, f_n)$) and outputting second intermediate signals.

The DC offset removal may be performed by a DC offset removal module.

In one embodiment, the circle estimation module is disposed between said sensor and said DC offset removal module, and said circle estimation operation is performed on a respective sensor signal ($\underline{y}(t, f_1) \ldots \underline{y}(t, f_n)$).

In another embodiment, said DC offset removal module is disposed between said sensor and the circle estimation module, and said circle estimation operation is performed on a respective modified signal ($\underline{y}'(t, f_1) \ldots \underline{y}'(t, f_n)$).

The transform module may comprises an averaging module, for receiving said second intermediate signals and deriving therefrom, the average over N receive channels of the radius value (R-value) of the circle estimation for the receive channels, and output third intermediate signals.

The processing circuitry may include a human detection module, operable for receiving the first intermediate signals ($\underline{A}_1 e^{-j2k_0 x_1(t)} \ldots \underline{A}_m e^{-j2k_0 x_m(t)}$) or for receiving the third intermediate signals and generating therefrom, the one or more occupancy status signals.

In one embodiment, said occupancy status signal comprises an occupant detection signal; and the human detection module is operable to generate and/or output (i) an occupant detection signal dependent upon a magnitude component of the first intermediate signals, (ii) a positive occupant detection signal when a sum of vectors derived from the magnitude component of the first intermediate signals is greater than a minimum threshold ($th_{min}$), and/or (iii) a negative occupant detection signal when a sum of vectors derived from the magnitude component of the first intermediate signals is less than a maximum threshold ($th_{max}$).

In one embodiment, said occupancy status signal comprises a vital signs signal; and the method comprises operating the processing circuitry for to generate and/or output the vital signs signal dependent upon a time-varying component ($x(t)$) of the first intermediate signals.

The processing circuitry may include a buffer strategy module, operable for applying a buffer strategy to the modified signals ($\underline{y}'(t, f_1) \ldots \underline{y}'(t, f_n)$), or signals based thereon, whereby hysteresis is exhibited by the one or more occupancy status signals.

The at least one occupiable position may comprise one a plurality of occupiable positions on a bench seat, and more preferably comprises 2 or 3 occupiable positions.

According to another aspect of the invention there is provided a recordable, rewritable or storable medium having recorded or stored thereon data defining or transformable into instructions for execution by processing circuitry and corresponding to at least the steps of any of claims 1 to 11 of the appended claims.

According to another aspect of the invention there is provided a server computer incorporating a communications device and a memory device and being adapted for transmission on demand or otherwise of data defining or transformable into instructions for execution by processing circuitry and corresponding to at least the steps of any of claims 1 to 11 of the appended claims.

In embodiments, rather than employing conventional CW radar for radar motion sensing, a frequency modulated CW (FMCW) radar is used, in order to obtain range information for the motion signal, whether it is in the interior or the exterior of the car cabin. A DC offset removal operation on every single frequency measurement allows static objects to be disregarded and for the system to focus on moving objects such as humans.

In embodiments, a general FMCW radar system with a static clutter removal algorithm is provided for in-vehicle occupant detection and classification (e.g. airbag suppression), for passenger presence detection, for passenger's vital sign monitoring and/or for seat-belt reminder functionality (SBR). In embodiments, the system includes an antenna system which illuminates one or more seats of an automotive vehicle. The transmitted signal is preferably frequency modulated in time. The radar system may comprise one or multiple receive channels, with one or two (or four) outputs (I/Q) per channel. The received signal may be mixed down with a single channel demodulator or an I/Q demodulator into the baseband. An advanced signal processing including an auto calibration routine and/or clutter removal may be used to detect occupants and their vital signs (e.g. breathing and heart beat) and to determine their distance to the radar system.

Due to the frequency modulation, range information of the moving object is obtained. Due to the cluttered and multi-reflection environment inside a car, the influence of static scatter is preferably subtracted by a DC offset removal operation on every single frequency measurement. A classification as to whether the object is inside or outside the car can be executed by range gating.

In embodiments, a general radar system with a static clutter removal algorithm is provided, for in-vehicle occupant detection and classification (e.g. for airbag suppression), for passenger presence detection and passenger's vital sign monitoring, and/or for seat-belt reminder functionality (SBR). The system includes an antenna system which illuminates one or more seats of an automotive vehicle. The transmitted signal is preferably frequency modulated in time. The radar system may comprise one or multiple receive channels with one or two (or four) outputs (I/Q) per channel. The received signal may be mixed down with a single channel demodulator or an I/Q demodulator into the baseband. An advanced signal processing including an auto calibration routine and/or clutter removal may be used to detect occupants and their vital signs (e.g. breathing and heart beat) and to determine their distance to the radar system.

BRIEF DESCRIPTION OF THE DRAWINGS

Embodiments of the invention will now be described by way of reference example to the accompanying drawings, in which.

DESCRIPTION OF PREFERRED EMBODIMENTS

Radar sensing within a complex environment like the interior of a car cabin is very challenging and the algorithm differs much from those for exterior radar sensing.

The advantage of radar systems is that in contrast to passive camera systems the radar system operates also in the night as it illuminates actively the scene. Active camera systems need an illumination in the light spectrum which can be visible for the human eye (compare to the glooming of infrared cameras). Radar systems work in the microwave range which is completely invisible for the human eye. In addition it penetrates into materials and can transmit through. So the integration behind plastic covers and textiles as well is possible while camera based systems need an opening to look through.

In one embodiment, the radar detection system has nearly fixed and constant antenna lobes over the whole frequency range from 24.00 GHz up to 24.25 GHz; however, the invention is not restricted to this frequency range. The frequency can be lower, higher or overlapping.

Conventional Doppler radars (CW-radars) are very sensitive and able to track small target motions within the micrometer range due to the Doppler Effect. Those radar systems are often used for door openers, motion/presence detectors but also for vital sign monitoring of the breathing and the seismocardiographic motions of the skin. CW radars are radiating electromagnetic waves of only one single frequency so the range of the moving targets cannot be determined and multiple targets cannot be separated. Due to the sensitivity CW-radars are recording all motions in the antenna beam. In order to measure dedicated object motions the operator has to ensure, that the antenna beam is only pointed to the object and that no other moving objects are visible for the radar system. This cannot be assured in the car interior, where the antenna lobe can be partially pointing outwards either directly or via multiple reflections. In embodiments, therefore, the range information needs is determined, in order to be able to distinguish whether the motion signal originated in the interior or the exterior of the car.

FMCW radars are in general able to determine the range of the targets due to a broadband frequency sweep for which the resolution improves with increasing bandwidth. The term resolution means here the minimal distance for which two targets can clearly be separated. For a FMCW radar working in the 24 GHz ISM band with a bandwidth of $\Delta f=250$ MHz the range resolution $\Delta R$ is 60 cm calculated with the following equation ($c_0$ is the speed of light in free-space):

$$\Delta R = \frac{c_0}{2\Delta f}$$

In the car exterior the targets' range and velocity are determined by single measurements of one increasing and one decreasing frequency ramp, both linearly.

$$R = \frac{c_0 T_c (f_{b2} - f_{b1})}{4\Delta f}$$

$$v = \frac{c_0 (f_{b2} - f_{b1})}{4 f_0}$$

The measured frequencies (beat frequencies $f_{b1}$ and $f_{b2}$) are differing because the high targets velocities induce Doppler shifts oppositely during the increasing and decreasing ramps. The chirp time $T_c$ is the duration of one ramp.

The velocity resolution is $$\Delta v = \frac{c_0}{2 f_0 T_c}$$

With breathing velocities of 1-2 cm/s the minimum chirp time needs to be 30-60 s for which the velocity must be constant. Thus, the small breathing velocities cannot be measured with conventional FMCW algorithms.

On the other hand, this allows the assumption that the body position is constant during a ramp measurement having duration of several milliseconds (which is not true for fast moving targets like cars or even airplanes). In the occupancy state monitoring according to embodiments of the invention, there will be no significant Doppler shift during on ramp measurement.

Another issue is that the recording of range values in a time series is not sufficiently accurate, due to the low range resolution and static cluttering.

The only way to yield the small body motion signal is to obtain the target's phase from the range domain in continuous FMCW mode or multiple-step FSK mode, or to evaluate the phases of each measured frequency in FSK mode. For each mode, the static clutter must be removed before occupancy analysis is completed.

In order to distinguish between each single seat with multiple input—multiple output (MIMO) and multiple input—single output (MISO) systems, several concepts are possible. These include the following.

Method A.

This involves spatial separation between each single seat is attained by very narrow antenna lobes of every radar channel. There is generally no interference between the single antennas. The main lobe is directly pointing at the middle of the seat. The advantage of this concept is that all sensors can be integrated in a decentralized manner, with arbitrary distances between the sensors (although the sensors should not face to each other).

Method B.

This involves Angle of arrival (AoA)/Direction of arrival (DoA): two or more antennas with broad radiation lobes are used. The antennas are printed on the same PCBs at a well-defined distance from each other. The targets have to be identified separately in each channel (e.g. by distance and/or by motion velocity) and the azimuthal direction is found by phase comparison. This is only possible when the objects are well separated by distance or have different velocities (for the best homogenous case constant velocities). In the case of rear-bench SBR all occupants are located at similar distances from the radar sensor, shoulder to shoulder and the breathing signal is nearly similar to each other. Thus, this concept is only suitable for a centralized version.

An occupancy state monitoring system according to embodiments of the invention has been implemented in accordance with Method A, in which 3 sensors are used in order to illuminate all seats on a rear bench of a car.

In the above given methods (Method A and Method B) every single antenna—whether in a centralized or decentralized version—requires electronics for the RF channels with one or two outputs per channel. In order to monitor the rear bench for 3 persons, in general 3 or more RF channels are necessary whether Method A (spatial separation) or Method B (AoA) is applied.

FIG. 1 is a schematic diagram of sensor positions within a passenger compartment of a vehicle for an embodiment of the invention. The position of sensor installation is preferably in front of the occupant, so that the whole area of the body or a part of it is illuminated. Possible integration places can be between top ceiling and car body, in the car body pillars, center console, overhead console, dash boards, steering wheel etc.

Figures 1A, 1B:
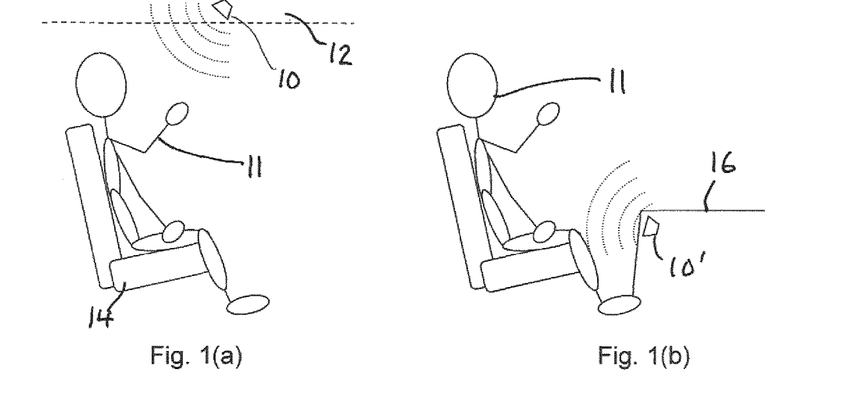
FIG. 1 is a schematic diagram of sensor positions within a passenger compartment of a vehicle for an embodiment of the invention.

FIG. 1(a) shows a radar sensor 10 built into the ceiling 12 of a vehicle. The sensor 10 includes at least one antenna (not shown) for illuminating one, two or three of the (occupiable) seating positions on the rear bench 14 of the vehicle, for detecting the presence of one or more occupants 11. FIG. 1b shows a radar sensor 10' for sensing occupancy in the front of the vehicle. In this case, the sensor 10' is built into front console 16, and includes at least one antenna (not shown) for illuminating one or both of the front seats of the vehicle.

In each case, the sensor 10, 10' may additionally include transmit-receive electronics and processing circuitry for carrying out the occupancy detection operations as discussed herein below, or the latter may be coupled to the antenna in sensor 10, 10', but located elsewhere within the vehicle.

The resolution (minimum range and minimum distance between two different targets) for range detection with FMCW (and also for pulse radars) is dependent upon the bandwidth of the RF signal:

$$\Delta R = \frac{c}{2 f_{BW}}$$

So, for the 24 GHz ISM band with 250 MHz bandwidth the resolution is 60 cm. In general the distance between the sensor 10 and occupants 11 is within that range, and the reflections from the A, B and C pillars, from the roof, seats, etc., are overlapping and result in a broad cluttering, such that the separate detection of occupants is barely possible. This means that with pure FMCW or pulse radar algorithms the occupants cannot be detected and resolved using the range information in such multi cluttering environment.

For this reason, motion sensing (e.g. with a pure continuous wave (CW) radar sensor) is a very stable method to track for occupants in multi cluttering and multipath environments. A pure CW radar sensor with only a single frequency is able to track a single target which is moving within a static environment. The amplitude of the Doppler signal is a quantity corresponding to the radar cross section (RCS) of the object, if the distance is known.

In this case, the static cluttering which results in a DC offset in the baseband is filtered out and the signal processing can focus on the motion information of the single target. The distance of the moving target is not determined with this method. A small object in close proximity of the sensor and a large object further away with equal motion yield similar base band signals $v_i^{I/Q}$. With such CW radar systems, it cannot be determined whether the signal results from motion in the interior or the exterior of the vehicle. This is an issue when the antenna lobes are pointing out of the windows.

Further problems arise when multiple targets are located in the field of view. When all objects are moving in the same manner the motion will be detected correctly.

In the case where the motion of multiple objects is homogeneous and the velocity differs clearly, the targets can also be separated by a Fourier transform of time series measurements. Thus, every target yields a separate Doppler shift in the frequency domain under the assumption of constant individual velocities.

However, multiple targets with different inhomogeneous motions (e.g. several humans breathing or different parts of the human body) cannot clearly be separated with a single antenna system (assuming no a-priori data is available). Methods such as "Blind Source Separation" are able to estimate different kinds of arbitrary motion in CW mode, but do not offer the reliability of the proposed invention, at least in embodiments.

On the other hand, a single target with an inhomogeneous periodic motion can "imitate" the signal of homogeneously moving targets.

To avoid this problem, a radar system with frequency adjustment (e.g. a VCO input) can be used to make a set of multiple CW motion measurements in time division multiplex—a so-called "multi tone FSK (frequency shift keying) modulation" or a "stepwise FMCW (frequency modulated continuous wave) modulation".

This can be interpreted as quasi-parallel measurement of the same target motions at the same time.

Figure 2:
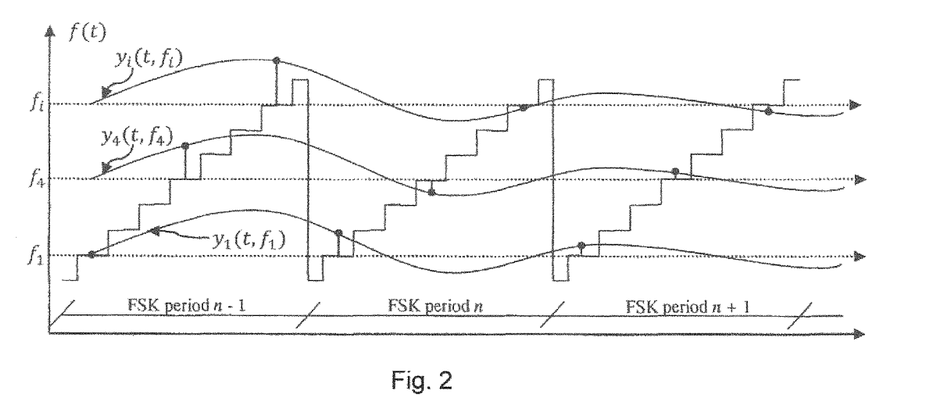
FIG. 2 illustrates the concept of Doppler measurement with multi tone FSK modulation, as used in embodiment of the invention.

FIG. 2 illustrates the concept of Doppler measurement with multi tone FSK modulation, as used in embodiment of the invention.

The steps of the multi tone FSK frequency need not be in ascending or descending order, but can be in arbitrary order. The frequency pattern used need only be repetitive for equidistant Doppler motion measurement in time.

If the single object motion is slow enough in comparison to the sampling rate, as is the case for human motions such as breathing or heartbeat, the Doppler signal at all frequencies is nearly similar at the sampling points (black dots in FIG. 2) in one FSK period n and is slightly changing from one FSK period to another.

Figure 3:
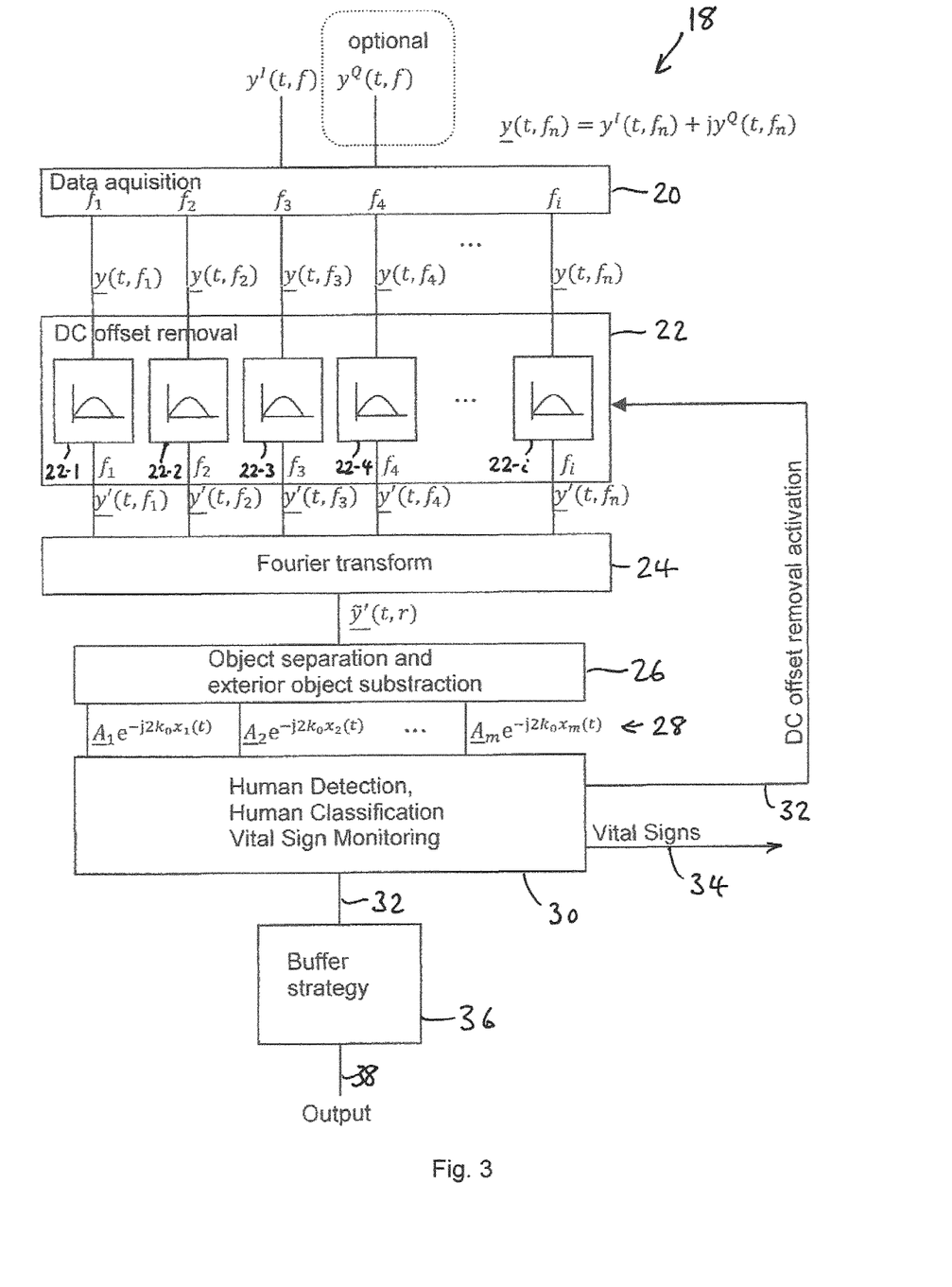
FIG. 3 is a block diagram of a complete radar signal processing routine for human detection and classification according to an embodiment of the invention.

FIG. 3 is a block diagram of a complete radar signal processing routine 18 for human detection and classification according to an embodiment of the invention. While reference is made to separate modules in FIG. 3, it will be appreciated by a person skilled in the art that such modules may be implemented as separate software modules, separate hardware modules, modules combining the functionalities of those separate modules, or combined hardware and software implementations of the described modules.

An input signal $\underline{y}(t, f_n)$ from the receive electronics (not shown) of the radar sensor 10, 10' of FIG. 1 is input to data acquisition module 20. At least the in-phase signal $y^1(t, f_n)$ is used by the system; however, optionally, the quadrature phase signal $jy^Q(t, f_n)$ may also be used in the embodiments of the invention.

Data acquisition module 20 separates the input signal $y^1(t, f_n)$ into a plurality of detection signals $\underline{y}(t, f_1)$ to $\underline{y}(t, f_n)$, one detection signal for each frequency (f1 to fi), in a manner known to a person skilled in the art.

The detection signals are fed to DC offset removal module 22, effectively comprising a plurality of band pass filters 22-1 to 22-i, one band pass filter for each frequency f1 to fi. The outputs of the band pass filters 22-1 to 22-i comprise modified signals $\underline{y}'(t, f_1)$ to $\underline{y}'(t, f_n)$, from which low frequency components of the detection signals have been removed.

Next, an FFT operation is performed on the modified signals by Fourier transform module 24. The result of the FFT is output by Fourier transform module 24 as composite (transform) signal $\underline{\tilde{y}}'(t, r)$, i.e. containing range information for the detected signals.

The composite signal $\underline{\tilde{y}}'(t, r)$ is input to object separation and exterior object subtraction module 26 which performs separation of objects and eliminates those objects that are, based on the detected ranges, external to the vehicle. In particular, module 26 may use range gating in order to eliminate from consideration those signals where the corresponding range is greater than the maximum possible to be within the vehicle.

The output of object separation and exterior object subtraction module 26 comprises time varying intermediate signals 28, i.e. signals ($\underline{A}_1 e^{-j2k_0 x_1(t)}$ to $\underline{A}_m e^{-j2k_0 x_m(t)}$) corresponding to candidate objects requiring further processing, which are input to human detection, classification and vital sign monitoring module 30 ("Human detection module 30"). Human detection module 30 is operable to output (32) a signal indicating whether, for each or one or more occupiable positions within the field of detection, an occupant is present in such position(s). In addition, human detection module 30 may be operable to output for feedback to DC offset removal module 22 a DC offset removal activation signal 32 that controls the activation and/or level of operation of the band pass filters 22-1 to 22-i of DC offset removal module 22.

Further, human detection module 30 may be operable to output a vital signs signal 34 for one, some, or all of the aforesaid occupiable positions.

In order to assure system function without undesirably frequent status changes, a buffer strategy module 36 is preferably employed which receives the output signal 32 from human detection module 30. The output 38 of buffer strategy module 36 provides a stabilized occupancy status signal that is the final output of the system.

In the following, the operation of the various modules in FIG. 3 will be discussed in greater detail.

A. DC Offset Removal

Here, the static DC offset at every frequency (e.g. resulting from frequency dependent electronic semiconductor offsets, direct antenna coupling and static clutter) is removed independently in the digitized baseband signals with one of the following methods.

Method 1: Conventional band pass filtering with pass frequencies between some tens of milliHertz and several tens of Hertz.

Method 2: Estimation of the centroid of the signal in the complex domain for I/Q signals and in the one-dimensional real domain for one channel signals (I only).

Method 3: Circle estimation method only for I/Q signals which form an orthogonal set of signals (e.g. the method described by Izhak Bucher).

Method 4: Taking the difference between two subsequent measurements.

Method 5: FFT of the complex I/Q signal or the pure real I signal.

Methods 1-5 require time series measurements and are always carried out in the complex domain. A good DC offset subtraction is only reached for the two first methods (Method 1 & Method 2), when the target motion amplitude is in the range of a half wavelength, so that the base band signals cover the full unambiguous range of the harmonic function (sine/cosine) and are completely rotating around in the complex domain. Method 3 implicitly requires a complex signal, but the DC offset is estimated correctly only with a fraction of the circle on the complex domain. If not available, the Hilbert transform to estimate a complex signal out of a pure real signal can offer a possible solution. Method 4 is the simplest one—with an immediate response after two measurements without the need to take a complete set of measurements into account. The main drawbacks are the inaccuracy when motion signal frequency is of the same order as the sampling frequency and the sensitivity to noise. A FFT DC offset removal can work theoretically with one single measurement in the frequency domain, but here a FFT on the time series measurement of each single frequency is intended.

B. Detection of Humans by Arbitrary Body Motion

Following filtering, the classification can now be done by
1. the power value (square sum, FFT amplitude, etc.) of the filtered signal (modified signals $\underline{y}'(t, f_1)$ to $\underline{y}'(t, f_n)$),
2. the variance of measurement points in the centroid calculation or
3. the radius value (R-value) of the circle estimation In theory, the detection and classification of a human is already possible with a pure CW radar system with the DC offset removal applied, but in practice the RCS of the human body is strongly dependent upon the contour and the frequency. For certain frequencies, negative interferences from wave contributions of different parts of the human body at the sensor antenna can decrease the circle radius/power value, while it increases at other frequencies or other postures of the human.

For this reason, multi frequency CW measurements provide an advantageous method to average the range of RCS deviations. A conceivable operation is the mean value calculation of all determined R-values at all frequencies (see FIGS. 9 and 10, discussed in further detail below).

The arbitrary body motion is not only the breathing motion but also the proper inertial motion due to motion of the car.

Although the range resolution at the 24 GHz ISM band is only 60 cm and objects in the car interior cannot be resolved, objects in the interior and exterior can be separated from the measurement which allows distinguishing between humans in the car cabin and approaching vehicles (with a large RCS).

The latter have to be subtracted before the calculation of the classification quantity. For this, the residual (DC offset removed) base band frequency signal is Fourier transformed (using Fourier transform module 24; FIG. 3) back to the time domain where the time values indicate the time of flight of the electromagnetic wave, which correlates directly with the range. The Fourier transform of one set of frequency measurements is called "range function".

Figure 4:
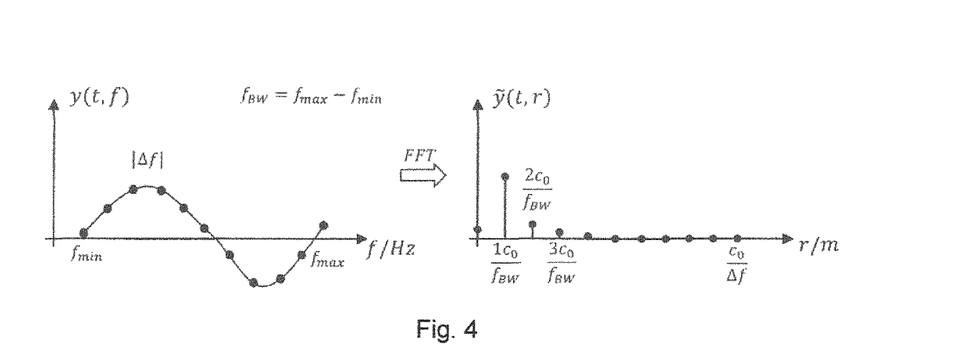
FIG. 4 illustrates the concept of range estimation by a Fourier transform, as used in embodiment of the invention.

FIG. 4 illustrates the concept of range estimation by a Fourier transform, as used in embodiment of the invention.

Targets are not clearly detectable as peaks in the range domain but as sinc-functions with a certain range width of 60 cm (first zero) due to the Fourier transform of a limited frequency range. Thus, there are still contributions overlapping in other ranges. A pure range filtering with a conventional low pass filter works for distant objects (overlapping spectral components are vanishing) but not for objects directly behind the car, whose sinc-maximum is lying in adjacent bins of the car interior in the range domain. All spectral contributions in a range higher than a certain threshold are preferably eliminated by function fitting of the sinc-function.

Again, the classification of humans is made according to power value, but now from the residual Fourier transform in the range domain or by classification Method 2 or Method 3 (see above) in the frequency domain by back transforming.

C. Range Estimation of the Human Body

After DC offset removal, the range of the moving target can be determined by the main peak in the Fourier transform in the limits of possible ranges (e.g. 0 m-1 m). In another embodiment, phase estimation of each single frequency measurement after DC offset removal is employed. This works only if one particular target is available after DC offset removal (target condition in FSK modulation). The target distance is found by the slope of a linear regression line.

D. Vital Sign Monitoring

Vital signs are not determined by the range estimation, but by monitoring the small signal motion which is included in the phase information. In every case, the residual frequency signal after DC offset removal is needed in order to guarantee correct phase estimation for the vital sign monitoring. There are multiple options for determining the vital sign signals of a human target
1. Determining the phase of every signal frequency measurement. For this, an I/Q demodulator is necessary in order to determine the phase on each single frequency. As mentioned above, this is a parallel multi Doppler measurement but requires that only one moving target is located in the antenna field of view. For one target with translational motion all Doppler signals are equal. If the object motion is complex (e.g. translation with rotation) or if several parts of the single target are moving separately (e.g. arm, chest and abdomen motion) the Doppler signal of every frequency differs slightly from each other. The variance of the Doppler signals is a quantity for the trustworthiness of the measured signal. For different breathing motions of the chest and abdomen when the person is sitting still (without any gestures), a mean or a median calculation of all Doppler signals results in a reliable vital sign signal.
2. Determining the phase of a range bin value of the Fourier transform in the range domain. In order to gain more range bins in the FFT, methods such as zero padding can be applied. This allows a finer resolution of the sinc functions in the range domain but does not change the dimension of the sinc function. The peak of the target-related sinc function is tracked, and the phase of this range bin is evaluated all range bins comprise the phase information of targets in this bin.

The determined phase signal comprises all motion from the arm, head, chest, abdomen, etc. The signal of the chest and the abdomen can be separated in relation to heart beat and breathing.

E. Separating Abdomen and Chest Motion

FIG. 5 is a plot of power value (received power) verses range, showing spectral contribution of body parts, and the sum of all in three, different scenarios.

Figure 5A:
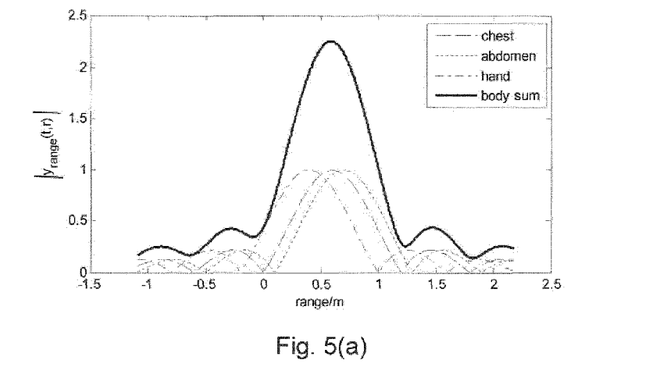
FIG. 5 is a plot of power value (received power) verses range, showing spectral contribution of body parts, and the sum of all, in three different detection scenarios.
Figure 5B:
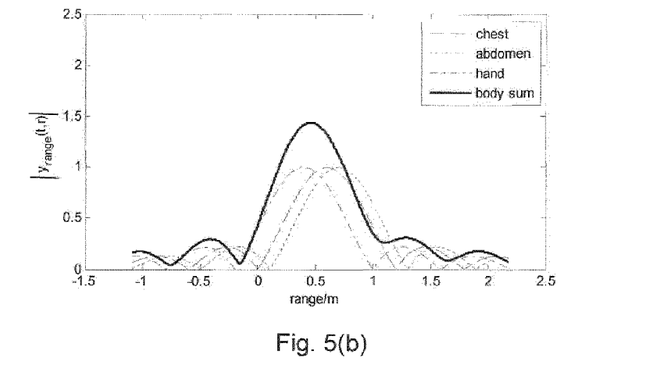
Figure 5C:
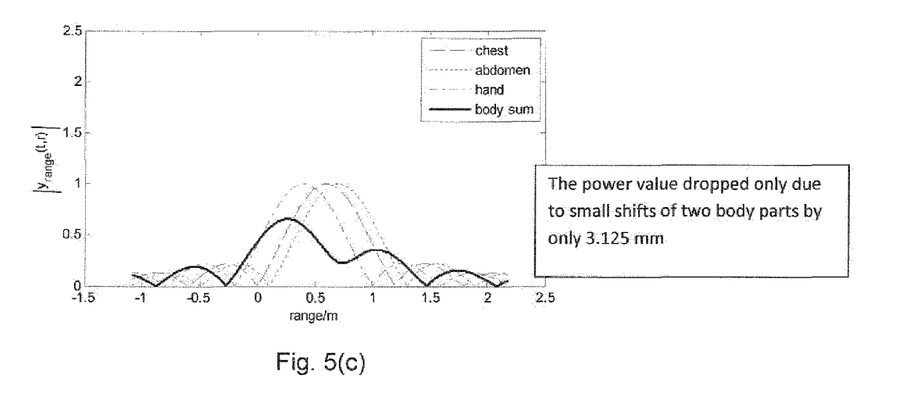

As the range bins of all body motions are adjacent, the analytical separation of the body parts is not possible within the Fourier transform in one calculation, as the resulting range function as the sum of all contributions (complex valued!) is still sinc-function like, as it is outlined in FIGS. 5(a) to (c). FIG. 5(a) shows the spectral contribution of chest (60 cm), abdomen (70 cm) and hand (40 cm) and the sum of all. FIG. 5(b) shows the spectral contribution of chest (60 cm), abdomen (70 cm+$\lambda$/4) and hand (40 cm) and the sum of all. FIG. 5(c) shows the spectral contribution of chest (60 cm), abdomen (70 cm+$\lambda$/4) and hand (40 cm+$\lambda$/4) and the sum of all.

For all three measurement sets, only one part is slightly changing by a quarter of the wavelength (3.125 mm).

It is obvious that, for several distance combinations, the power of the signal is reduced which implies problems if the power of one single range signal is used for the human occupant detection.

There exists a possibility to estimate the body part contributions in one single set of frequency measurements using the so-called "spectral estimators", such as with, e.g., the MUSIC or ESPRIT algorithm, which offer a kind of "super-resolution". These methods can be applied in order to estimate the position of the moving body parts and to fit a set of sinc-functions to the measured range function. Now the phase of the fitted complex sinc functions can be evaluated as motion information of each single body part and processed for vital sign monitoring.

In another embodiment, separation of close-by body parts is achieved by a time series recording of a set of range functions. As the shape of the resulting overall sum function of all body part contributions is changing over the time, the position of all body parts can be estimated by characteristics of the sinc-function.

In another embodiment, a so-called "independent component analysis" (ICA) which separates statistically the different complex contributions and their phase changes over time is used. This method may be successfully applied in the range domain, but also in the frequency domain directly.

Figure 6:
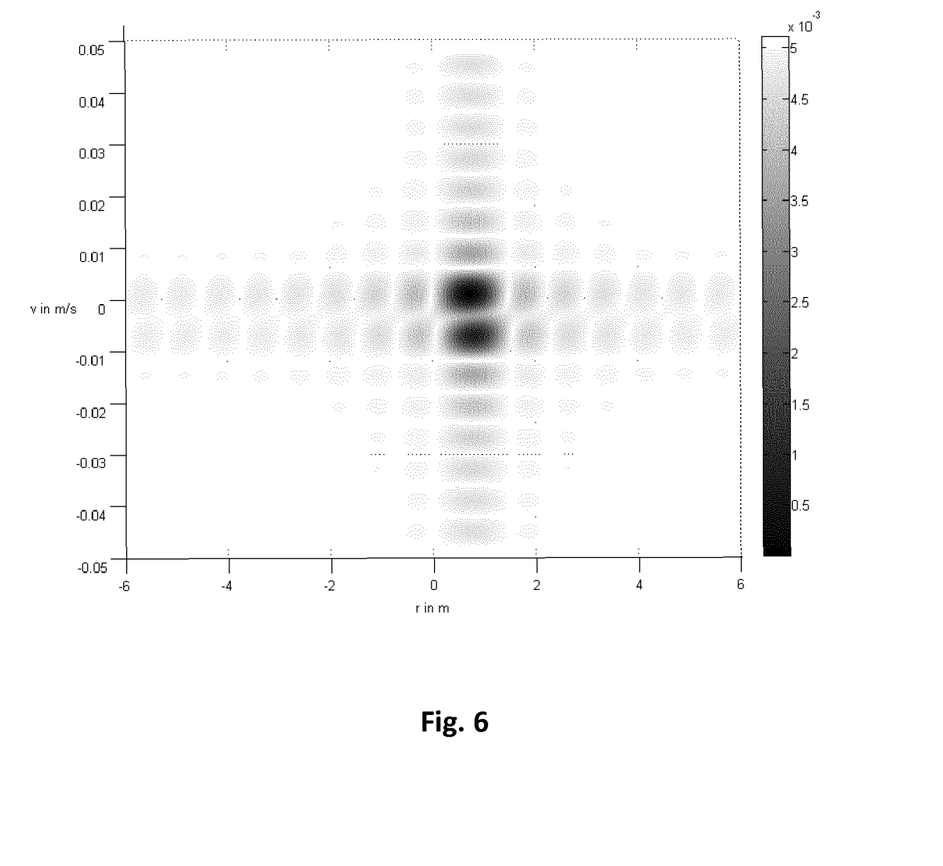
FIG. 6 is a plot of velocity vs range, showing diverging peaks produced by stepwise 2D-FFT of received signal.

In another embodiment, a method used for separating the single body parts is a stepwise 2D-FFT, where (i) the first FFT stands for the transformation of each single FSK measurement for the frequency domain into the range domain and (ii) the second FFT transforms the time series record of the range data into the velocity range. In instances where several body parts are moving differently, this can be distinguished while the peaks in the 2D plane are separating. By means of peak tracking, the body parts motions can be determined by phase evaluation of the tracked peaks.

FIG. 6 is a plot of velocity vs range, showing diverging peaks produced by stepwise 2D-FFT of received signal.

In another embodiment, separating close-by body parts is by means of time series recording of a set of range functions. As the shape of the resulting overall sum function of all body part contributions is changing over the time the position of all body parts can be estimated by characteristics of the sinc-function.

Now the phase of the fitted complex sinc functions can be evaluated as motion information of each single object and processed for vital sign monitoring.

F. Enhanced Human Detection

In addition to the method given in section B above, where the power value or signal radius is evaluated for every single CW measurement (N values) over a time series while those are moving, the human can now also be detected by checking whether the amplitudes of the body parts (sinc functions) are above a predefined threshold in one or multiple single range measurements, and whether their distance information is within a certain range.

According to a preferred embodiment, a three value output is created by the introduction of a two limit thresholds [$th_{min}$ $th_{max}$]. If power value is above the maximum threshold $th_{max}$ a human is detected for sure. If below the minimum threshold $th_{min}$ the seat is unoccupied. If the power value is between both thresholds the occupancy detection is "not sure".

Figure 7:
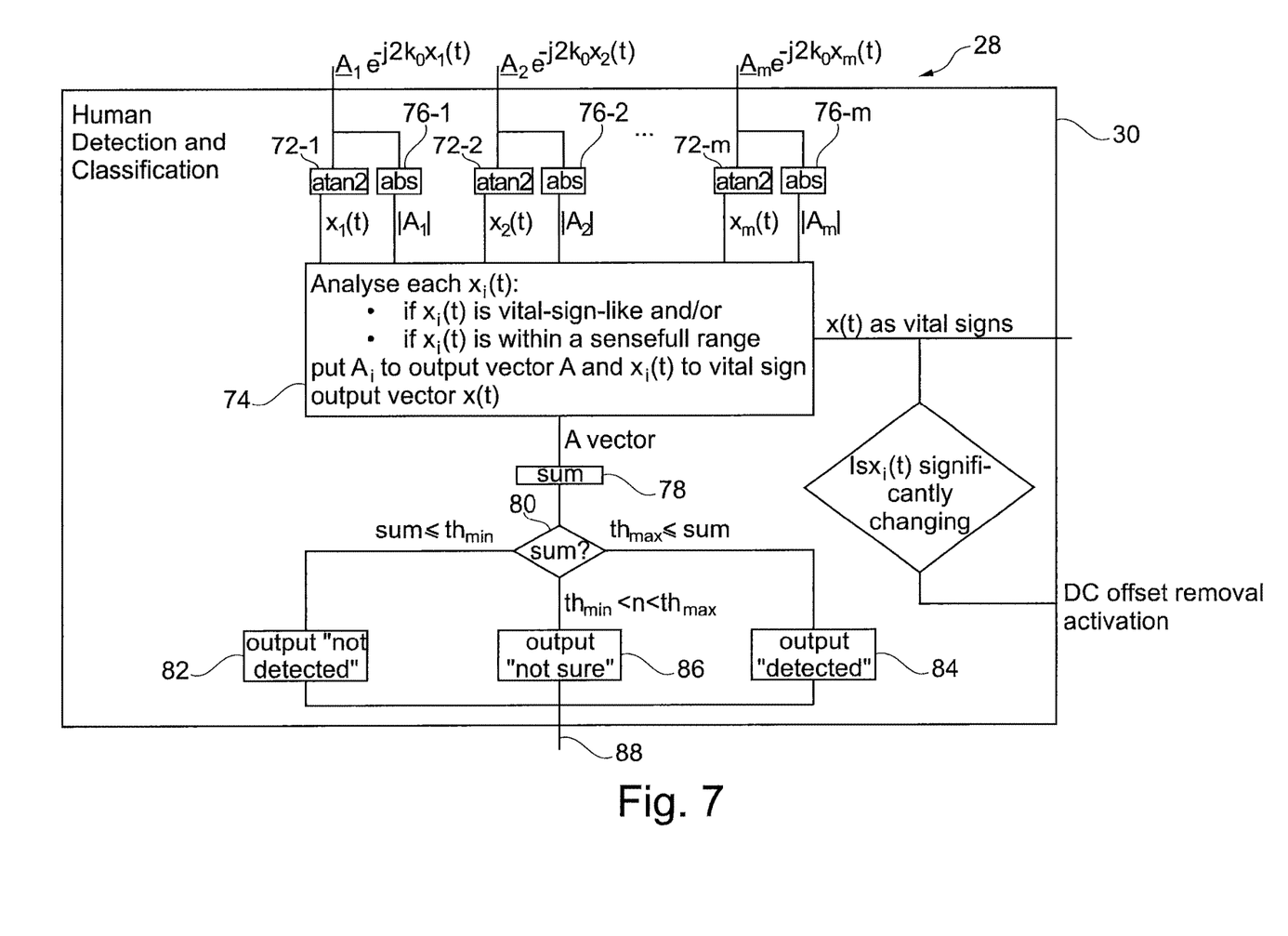
FIG. 7 is a block diagram of the signal processing for human detection and classification according to an embodiment of the invention.

FIG. 7 is a block diagram of the signal processing for human detection and classification according to an embodiment of the invention.

As mentioned above, human detection module 30 receives a plurality of intermediate signals (28; FIG. 3) in the time domain. Preferably, human detection module 30 includes, for each intermediate signal, an a tan 2 (arc tangent with 2 arguments) operator 72-1 to 72-$m$ that outputs a time varying range signal ($x_1(t)$) to ($x_m(t)$) that is input to analysis module 74. In addition, for each intermediate signal 28, an absolute value operator 76-1 to 76-$m$ is provided, that outputs the modulus ($|A_1|$ to $|A_m|$) of the intermediate signals 28.

Analysis module 74 is then operable to output a modulus vector A based on the Ais, and to output vector x(t), i.e. a vital sign vector based on the xi(t) components.

A test is made at 80 to determine whether the sum derived at 78 is less than or equal to a minimum threshold, in which case a "not detected" signal is output (82) by human detection module 30. Alternatively, if it is determined that the sum is greater than a maximum threshold, a "detected" signal is output (84) by the human detection module 30; otherwise, i.e. with the sum (n) lying between the minimum threshold ($th_{min}$) and the maximum threshold ($th_{max}$), a "not sure" signal is output (86) by the human detection module 30 at output 88.

In the following, a typical situation of occupant detection is described: it is assumed that there is an empty seat in a car vehicle. Due to the DC offset removal of each single frequency and the static characteristic of all objects, the output of the filtering is a flat zero line. Items such as the backrest and the seating are static and are also eliminated by the DC offset removal.

If a person enters the car and is sitting on the seat, the band pass filter/DC offset removal is directly reacting and immediately exhibits a change in signal. The human detection method described in section B above gives an output indicating that something which is moving is located on the seat. This can activate, e.g., a seat belt reminder (SBR) signal or contribute to a buffer which activates the SBR signal after a certain time. While the backrest and the seating are now hidden, it contributes now firstly to the residual signal as a new DC offset, but with negative sign (because they are now missing). This does not affect the method in section B above, as this method only looks at the power value/radius of the changing signal.

After elapse of the time constant of the DC offset removal algorithm, the "negative contributions" of the backrest and seating are eliminated again.

If the occupant now holds their breath, the method of section B above will lose the detection, as the considered time series values on every frequency are no longer changing. Thus, a frequency dependent curve is remaining.

The addition now of the methods of sections C to E above allows measurement of the amplitudes of all objects on the remaining frequency curve. From the amplitude, the algorithm knows that there is a static object remaining on the seat. Due to the distance information (assume, for example, 65 cm), it is obvious that it is not the rear bench.

If the person now stops breathing completely for some time constants of the filter (more than 30 sec), the amplitude of the frequency curve will decrease over time to the above mentioned flat zero line in the beginning, and the detection will also be lost.

Instead, the situation is similar to the one of keeping the breath when the occupant is leaving the seat, but here the sensor detects the backrest and the seating as static objects by their amplitude. However, due to the distance information, the system knows that the seat is unoccupied. Also, after a certain time, the frequency curve vanishes.

In order to avoid the vanishing of the frequency curve, a switch (DC offset removal activation 32 in FIG. 3) can be implemented which deactivates the DC offset removal if no change in the CW measurements of method of section B above is occurring.

G. Human Classification

For human classification, the vital sign signals themselves are processed in order to classify whether a live subject (occupant) is present on the seat. If the vital sign is periodic and similar to breathing motion, the occupant is classified as human. For this reason, a FFT, a spectral estimator or autocorrelation methods can be applied to detect the breathing information.

Furthermore, heart beats can be detected in the same manner by the vital sign signal. In the case of a standing and closed car, if a heartbeat is detected in the car an alarm can be given, or the car windows can be opened, when temperature rises in the car, in order to avoid occupants suffering hyperthermia. This is an additional possible application of the radar sensor. For security reasons, the "simple" human detection of section B above should not activate the opening of windows as it is not robust enough; however, the more sophisticated human classification may be allowed to do so.

H. Buffer Strategy

Figure 8:
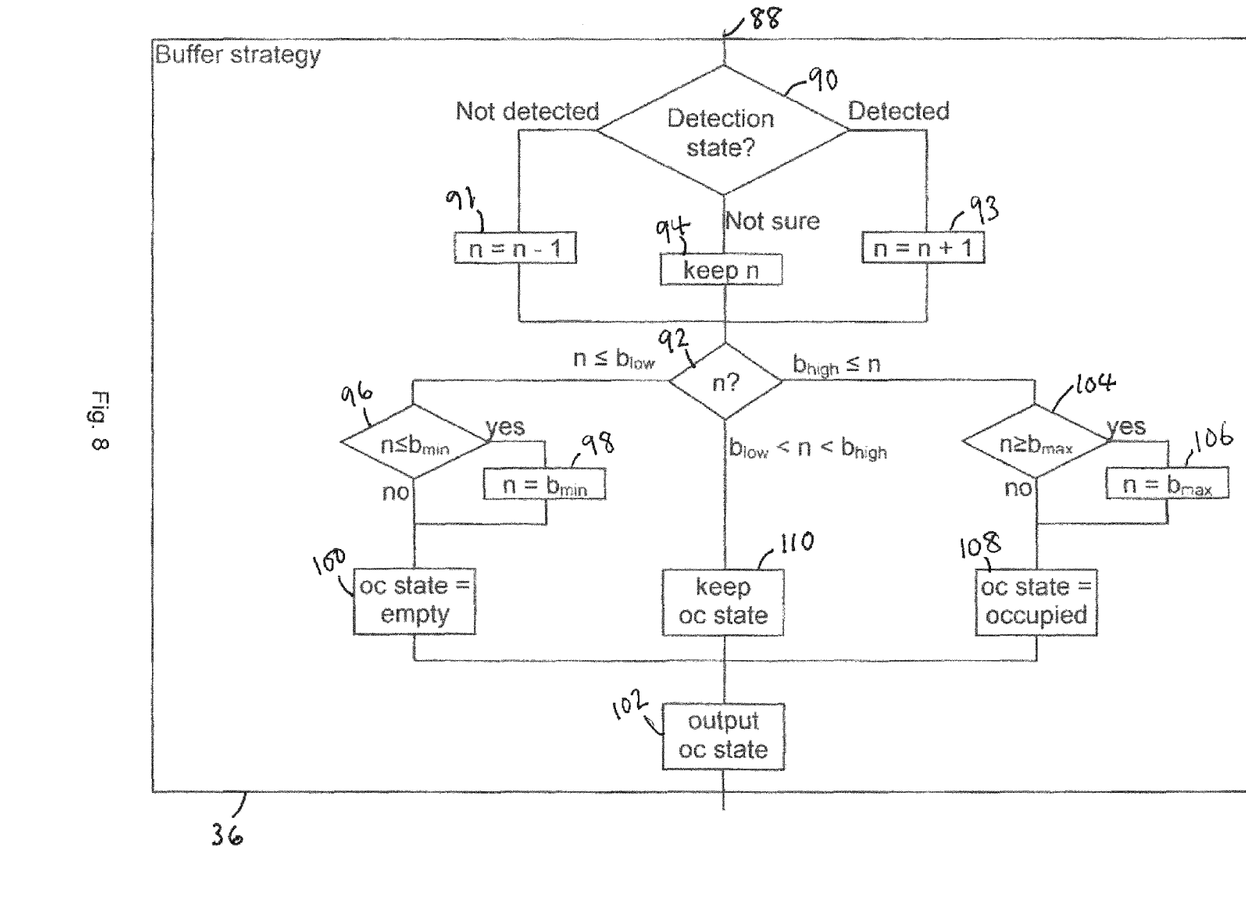
FIG. 8 is a block diagram of the buffer strategy for human detection and classification, according to an embodiment of the invention.

FIG. 8 is a block diagram of the buffer strategy for human detection and classification, according to an embodiment of the invention. The buffer strategy module 36 receives as input the output 88 of human detection module 30 (FIG. 7).

As seen in FIG. 8, at 90 the nature of the received signal is determined: if the detection state is "not detected", the sum counter n is decremented by 1 at 91, and the processing continues at 92. If, on the other hand, the detection state is determined at 90 to be "detected" (i.e. indicating that a person was detected in the corresponding occupiable position), the sum counter n is incremented by 1 at 93, and processing continues at 92. Otherwise, if the signal input to buffer strategy module 36 was a "not sure" detection state, the sum counter n is retained at 94, and processing proceeds at 92.

At 92, a determination is made as to whether sum counter n lies within a lower range (i.e. below threshold blow). If so, a determination is made at 96 as to whether counter sum n is less than or equal to a minimum stability threshold (bmin), and if so, n is assigned to the lower stability threshold bmin at 98. If not, the occupancy state is assigned to "empty" (indicating that there is no occupant in the occupiable position) at 100, and output at 102 by the buffer strategy module 36.

On the other hand, if it is determined at 92 that the sum counter n lies within an upper range (greater than bhigh), then processing continues at 104. Here, a further determination is made as to whether sum counter n is greater than or equal to an upper stability threshold (bmax), and if so, sum counter n is assigned the value of the upper threshold (bmax) at 106. Then, as a consequence, at 108 the occupancy state is assigned the value "occupied" (indicating that there is an occupant within the occupiable position) and this occupancy state is output at 102.

Finally, if it is determined at 92 that the sum counter n lies between the lower range and the upper range (i.e. $b_{low}$ is less than $b_{high}$), the current occupancy state is retained at 110, and that occupancy state is output at 102.

In embodiments, the buffer strategy may comprise a single threshold bon/off or a two value threshold [$b_{low}$ $b_{high}$] in order to implement a hysteresis.

I. Advanced Features

If the human body parts can clearly be separated by range by the tracking of their motions (according to sections B to G above) the motion of the hand can be used as input (as gestures) for a man-machine interface. One application can be to switch on the reading light of the particular occupant.

Fault detection may be provided—if a hand is blocking the sensor or if somebody is passing the sensor when entering or leaving the car—and this can enhance the robustness of the sensor.

J. Alternative Embodiments of the Invention

In this document, several embodiments are outlined. The embodiment used is strongly dependent on the cost, but also the reliability of the particular application. All possible combinations of above described signal processing routines are contemplated. The invention is not related to a particular embodiment but encompasses a diversity of possible embodiments.

Figure 9:
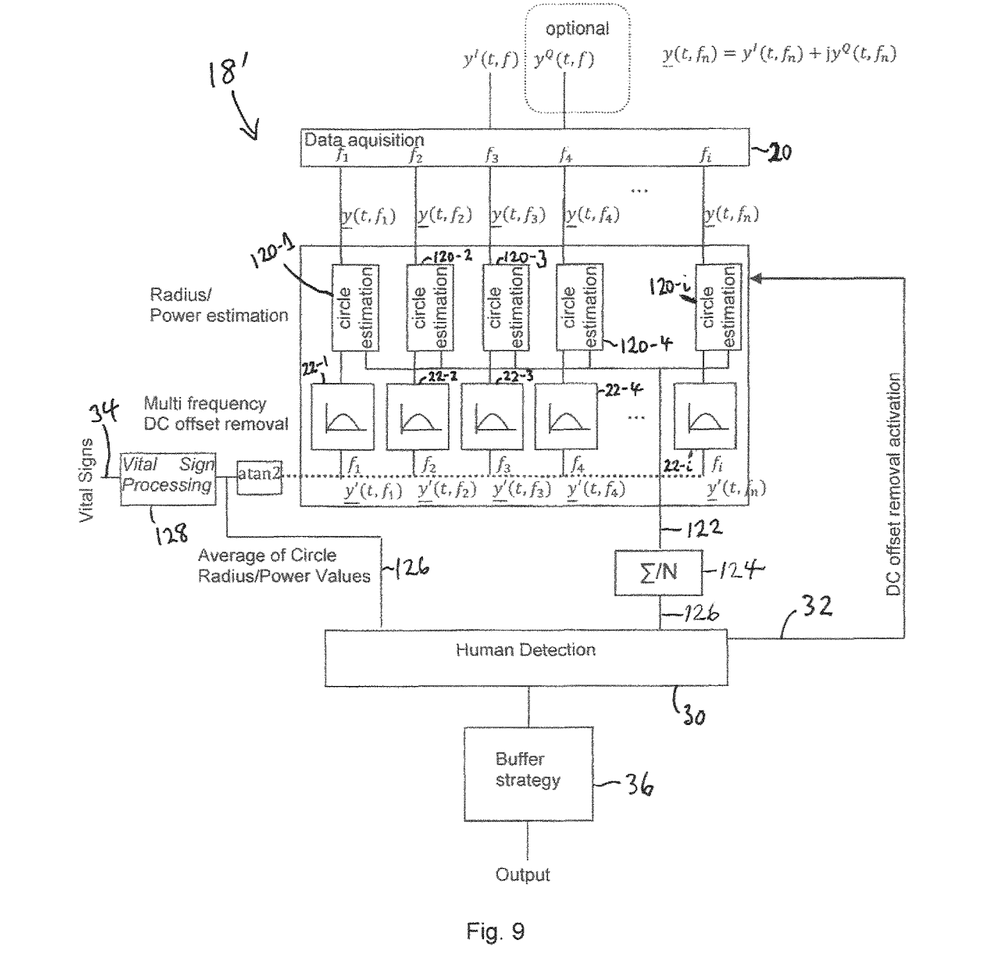
FIG. 9 is a block diagram of a complete radar signal processing routine according to a further embodiment of the invention with circle/power estimation and DC offset removal in one step.

FIG. 9 is a block diagram of a complete radar signal processing routine 18' according to a further embodiment of the invention—with circle/power estimation and DC offset removal in one step. This is the same as the embodiment of FIG. 3, except as described in the following.

In this embodiment, there are provided, for each frequency ($f_1$ to $f_i$), a circle estimation module 120-1 to 120-$i$. In this embodiment, the circle estimation modules 120-1 to 120-$i$ are disposed between data acquisition module 10 and band pass filters 22-1 to 22-$i$. For a given frequency ($f_1$ to $f_i$), circle estimation modules 120-1 to 120-$i$ perform radius-power estimation in relation to received detection signal y(t, $f_1$) to ỹ y(t, $f_n$).

As well as being provided to band pass filters 22-1 to 22-$i$, the circle estimation outputs 122 are provided to summing/averaging module 124. The latter performs averaging of the circle radius/power values and provides averaged signals 126 to human detection module 30.

The average of the circle radius/power values signal 126 is provided to a vital signs processing module 128, which is operable to generate, based thereon, a vital signs output signal 34. The vital signs processing module 128 may also receive an input comprising the result of an a tan 2 operator 130 on the modified signals (ỹ y'(t, $f_1$) to ỹ y(t, $f_n$)) that are output by band pass filters 22-1 to 22-$i$.

Figure 10:
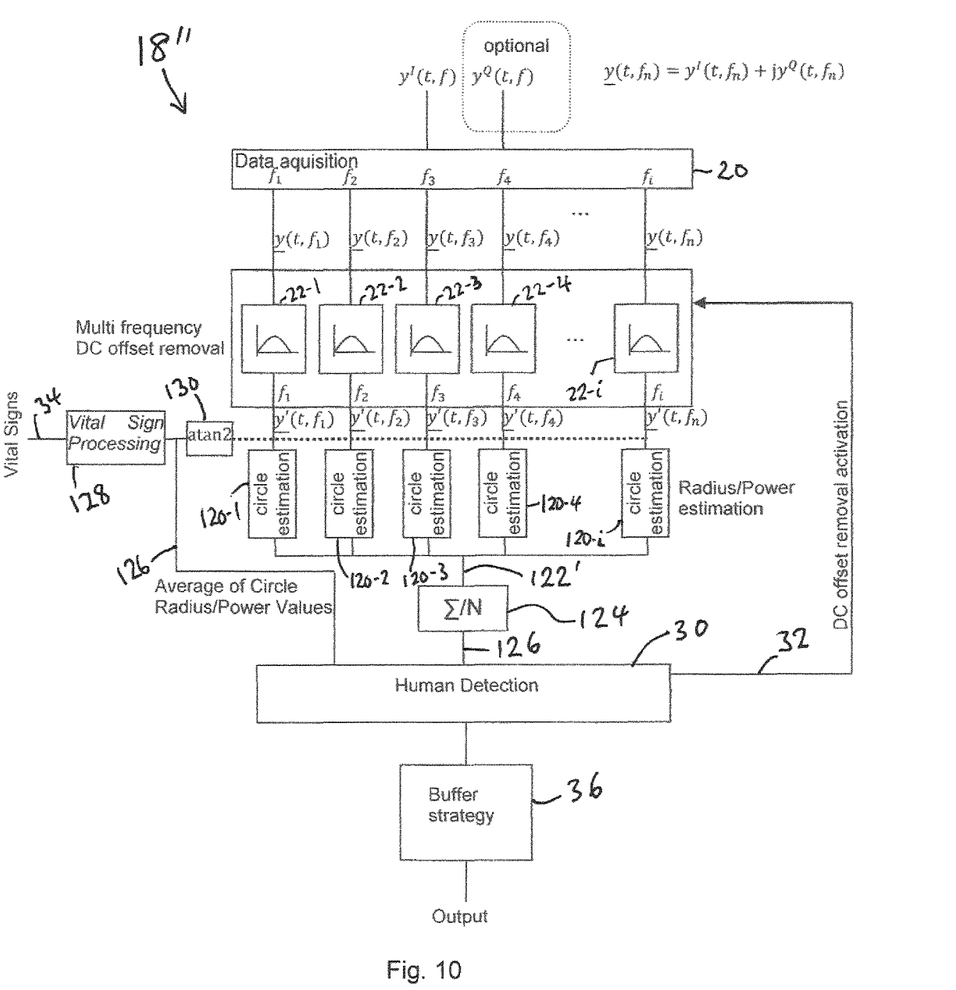
FIG. 10 is a block diagram of a complete radar signal processing routine according to a yet further embodiment of the invention with circle/power estimation and DC offset removal in two steps.

FIG. 10 is a block diagram of a complete radar signal processing routine 18" according to a yet further embodiment of the invention—with circle/power estimation and DC offset removal in two steps. This is the same as the embodiment of FIG. 9, except as described as follows. In this embodiment, the band pass filters 22-1 to 22-$i$ are disposed between data acquisition module 20 and circle estimation modules 120-1 to 120-$i$. Otherwise, the operation is the same as that of the embodiment of FIG. 9, and therefore will not be discussed in detail.

While embodiments have been described by reference to embodiments having various components in their respective implementations, it will be appreciated that other embodiments make use of other combinations and permutations of these and other components.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit and scope of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A method for sensing occupancy status within an automotive vehicle using a radar sensor system, the radar sensor system comprising an antenna system, at least one sensor and processing circuitry, the method comprising:
   illuminating, using the antenna system, at least one occupiable position within the vehicle with continuous wave (CW) signals, the CW signals being frequency modulated in time;
   receiving, using the at least one sensor, at least one sensor signal reflected as a result of the CW signals, the at least one sensor including a plurality of receive channels, each channel having a different frequency;
   applying, using the processing circuitry, for each receive channel, DC offset removal to the corresponding sensor signal to generate a modified signal; and
   generating, using the processing circuitry, based on the modified signals, one or more occupancy status signals, the occupancy status signal indicating a property related to said at least one occupiable position.

2. The method of claim 1, wherein the one or more occupancy status signals comprise at least one of:
   an occupant detection signal, indicating whether or not an occupant is present in the occupiable position,
   an occupant classification signal, indicating a classification for an occupant present in the occupiable position, or
   an occupant vital signs signal, indicating the extent to which vital signs are exhibited by an occupant in the occupiable position.

3. The method of claim 1, further comprising generating, using the processing circuitry, a composite signal based on the sensor signals from all receive channels.

4. The method of claim 3, further comprising generating, using the processing circuitry, a plurality of first intermediate signals in the time domain from the composite signal, each first intermediate signal corresponding to a candidate object.

5. The method of claim 4, further comprising performing, using the processing circuitry, object separation and exterior object subtraction on said composite signal to separate and eliminate objects that are external to the vehicle.

6. The method of claim 5, further comprising performing, using the processing circuitry, for each channel, a circle estimation operation on a signal comprising or based upon a respective sensor signal and outputting second intermediate signals.

7. The method of claim 6, further comprising performing, using the processing circuitry, the circle estimation before said DC offset removal, whereby said circle estimation operation is performed on a respective sensor signal, or performing said DC offset removal before the circle estimation, whereby said circle estimation operation is performed on a respective modified signal.

8. The method of claim 6, further comprising receiving, using the processing circuitry, said second intermediate signals and deriving therefrom, the average over N receive channels of a radius value of the circle estimation for the receive channels, and output third intermediate signals.

9. The method of claim 4, further comprising receiving, using the processing circuitry, the first intermediate signals or for receiving third intermediate signals and generating therefrom, the one or more occupancy status signals.

10. The method of claim 9, wherein:
   (a) said occupancy status signal comprises an occupant detection signal; and the method comprises operating the processing circuitry to generate:
      (i) an occupant detection signal dependent upon a magnitude component of the first intermediate signals,
      (ii) a positive occupant detection signal when a sum of vectors derived from the magnitude component of the first intermediate signals is greater than a minimum threshold, or
      (iii) a negative occupant detection signal when a sum of vectors derived from the magnitude component of the first intermediate signals is less than a maximum threshold,
   (b) said occupancy status signal comprises a vital signs signal; and the method comprises operating the processing circuitry to generate the vital signs signal dependent upon a time-varying component of the first intermediate signals.

11. The method of claim 1, comprising applying, using the processing circuitry, a buffer strategy to the modified signals, or signals based thereon, to stabilize the one or more occupancy status signals wherein the buffer strategy implements a hysteresis using a two value threshold.

12. A programmable radar sensor system for sensing an occupancy status within an automotive vehicle, the radar sensor system comprising:
   an antenna system configured to illuminate at least one occupiable position within the vehicle with continuous wave (CW) signals, the CW signals being frequency modulated in time;
   at least one sensor configured to receive at least one sensor signal reflected as a result of the CW signals, the at least one sensor including a plurality of receive channels, each channel having a different frequency; and processing circuitry configured to:
apply for each receive channel, DC offset removal to the corresponding sensor signal to generate a modified signal; and
generate based on the modified signals, one or more occupancy status signals that indicate a property related to said at least one occupiable position.

13. A radar sensor system for sensing occupancy status within an automotive vehicle, the system comprising:
an antenna system, for illuminating at least one occupiable position within the vehicle with continuous wave (CW) signals, the CW signals being frequency modulated in time;
at least one sensor for receiving at least one sensor signal reflected as a result of the CW signals, the at least one sensor including a plurality of receive channels, each channel having a different frequency;
processing circuitry, coupled to the at least one sensor, the processing circuitry being configured to:
apply, for each receive channel, DC offset removal to the corresponding sensor signal to generate a modified signal; and
generate, based on the modified signals, one or more occupancy status signals, the occupancy status signal indicating a property related to said at least one occupiable position.

14. A non-transitory computer readable medium having instructions stored thereon which, when executed, cause processing circuitry to:
receive, using at least one sensor, at least one radar sensor signal reflected as a result of continuous wave signals from an antenna system configured to illuminate at least one occupiable position within a vehicle, the continuous wave signals being frequency modulated in time, wherein the at least one sensor includes a plurality of receive channels, each channel having a different frequency;
apply, for each receive channel, a DC offset removal to the at least one radar sensor signal to generate a modified signal; and
generate, based on the modified signals, one or more occupancy status signals that indicate a property related to said at least one occupiable position.

* * * * *